(12) United States Patent
Armstrong et al.

(10) Patent No.: US 8,454,694 B2
(45) Date of Patent: Jun. 4, 2013

(54) INTERBODY DEVICE AND PLATE FOR SPINAL STABILIZATION AND INSTRUMENTS FOR POSITIONING SAME

(75) Inventors: William Armstrong, Memphis, TN (US); Thomas Carls, Memphis, TN (US); John A. Cowan, Rome, GA (US); James Duncan, Hernando, MS (US); Richard A. Hynes, Melbourne Beach, FL (US); Anthony J. Melkent, Memphis, TN (US); Jean-Pierre Mobasser, Indinaapolis, IN (US); D. Hal Silcox, Atlanta, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 60 days.

(21) Appl. No.: 13/040,035

(22) Filed: Mar. 3, 2011

(65) Prior Publication Data
US 2012/0226319 A1    Sep. 6, 2012

(51) Int. Cl.
*A61F 2/44*    (2006.01)

(52) U.S. Cl.
USPC ......................................................... 623/17.11

(58) Field of Classification Search
CPC ....................................................... A61F 2/44
USPC ............ 606/246, 249, 279, 280, 70, 71, 281, 606/286, 287, 289, 295, 99, 86 A, 86 B; 623/17.11, 17.16
See application file for complete search history.

(56) References Cited

U.S. PATENT DOCUMENTS

| 4,599,086 A | 7/1986 | Doty, Jr. |
| 4,657,550 A | 4/1987 | Daher |
| 4,834,757 A | 5/1989 | Brantigan |
| 4,878,915 A | 11/1989 | Brantigan |
| 4,904,261 A | 2/1990 | Dove et al. |
| 4,955,908 A | 9/1990 | Frey et al. |
| 5,192,327 A | 3/1993 | Brantigan |
| 5,290,312 A | 3/1994 | Kojimoto et al. |
| 5,306,309 A | 4/1994 | Wagner et al. |
| 5,364,399 A | 11/1994 | Lowery et al. |
| 5,397,364 A | 3/1995 | Kozak et al. |
| 5,405,391 A | 4/1995 | Hednerson et al. |
| 5,425,772 A | 6/1995 | Brantigan |
| 5,443,514 A | 8/1995 | Steffee |
| 5,514,180 A | 5/1996 | Heggeness et al. |
| 5,571,190 A | 11/1996 | Ulrich et al. |
| 5,716,415 A | 2/1998 | Steffee |
| 5,766,252 A | 6/1998 | Henry et al. |
| 5,865,845 A | 2/1999 | Thalgott |

(Continued)

FOREIGN PATENT DOCUMENTS

EP    0 826 376 A1    4/1998

*Primary Examiner* — Eduardo C Robert
*Assistant Examiner* — David Comstock

(57) ABSTRACT

Systems, methods and devices for providing stabilization between first and second vertebrae are provided. More particularly, in one form a system includes an implant configured to be positioned in a disc space between the first and second vertebrae and a freestanding plate for engagement with extradiscal surfaces of the first and second vertebrae. The system also includes an insertion instrument with an engaging portion configured to releasably engage with the implant and the plate such that the implant and plate can be positioned together relative to the first and second vertebrae. In one aspect, an angular orientation of the implant relative to the plate is adjustable when the implant and the plate are engaged by the instrument. In this or another aspect, the implant and plate are held in a contiguous relationship when engaged by the instrument. However, different forms and applications are also envisioned.

23 Claims, 10 Drawing Sheets

U.S. PATENT DOCUMENTS

| | | |
|---|---|---|
| 5,888,223 A | 3/1999 | Bray, Jr. |
| 5,888,224 A | 3/1999 | Beckers et al. |
| 5,888,227 A | 3/1999 | Cottle |
| 5,916,267 A | 6/1999 | Tienboon |
| 5,984,922 A | 11/1999 | McKay |
| 5,989,290 A | 11/1999 | Biedermann et al. |
| 6,015,436 A | 1/2000 | Schönhöffer |
| 6,066,175 A | 5/2000 | Henderson et al. |
| 6,086,613 A | 7/2000 | Camino et al. |
| 6,090,143 A | 7/2000 | Meriwether et al. |
| 6,096,080 A | 8/2000 | Nicholson et al. |
| 6,106,557 A | 8/2000 | Robioneck et al. |
| 6,120,503 A | 9/2000 | Michelson |
| 6,156,037 A | 12/2000 | Lehuec |
| 6,158,245 A | 12/2000 | Savant |
| 6,159,211 A | 12/2000 | Boriani et al. |
| 6,176,881 B1 | 1/2001 | Schär et al. |
| 6,176,882 B1 | 1/2001 | Biedermann et al. |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,228,085 B1 | 5/2001 | Theken et al. |
| 6,235,059 B1 | 5/2001 | Benezech et al. |
| 6,241,769 B1 | 6/2001 | Nicholson et al. |
| 6,245,108 B1 | 6/2001 | Biscup |
| 6,277,149 B1 | 8/2001 | Boyle et al. |
| 6,342,074 B1 | 1/2002 | Simpson |
| 6,375,681 B1 | 4/2002 | Truscott |
| 6,395,030 B1 | 5/2002 | Songer et al. |
| 6,419,705 B1 | 7/2002 | Erickson |
| 6,428,575 B2 | 8/2002 | Koo et al. |
| 6,432,106 B1 | 8/2002 | Fraser |
| 6,443,987 B1 | 9/2002 | Bryan |
| 6,454,806 B1 | 9/2002 | Cohen et al. |
| 6,458,159 B1 | 10/2002 | Thalgott |
| 6,461,359 B1 | 10/2002 | Tribus et al. |
| 6,482,233 B1 | 11/2002 | Aebi et al. |
| 6,485,517 B1 | 11/2002 | Michelson |
| 6,500,205 B1 | 12/2002 | Michelson |
| 6,500,206 B1 | 12/2002 | Bryan |
| 6,503,279 B1 | 1/2003 | Webb et al. |
| 6,508,818 B2 | 1/2003 | Steiner et al. |
| 6,520,993 B2 | 2/2003 | James et al. |
| 6,527,805 B2 | 3/2003 | Studer et al. |
| 6,558,387 B2 | 5/2003 | Errico et al. |
| 6,558,423 B1 | 5/2003 | Michelson |
| 6,562,073 B2 | 5/2003 | Foley |
| 6,576,017 B2 | 6/2003 | Foley et al. |
| 6,579,290 B1 | 6/2003 | Hardcastle et al. |
| 6,585,740 B2 | 7/2003 | Schlapfer et al. |
| 6,592,624 B1 | 7/2003 | Fraser et al. |
| 6,629,998 B1 | 10/2003 | Lin |
| 6,635,086 B2 | 10/2003 | Lin |
| 6,635,087 B2 | 10/2003 | Angelucci et al. |
| 6,652,584 B2 | 11/2003 | Michelson |
| 6,666,889 B1 | 12/2003 | Commarmond |
| 6,673,075 B2 | 1/2004 | Santilli |
| 6,676,703 B2 | 1/2004 | Biscup |
| 6,682,561 B2 | 1/2004 | Songer et al. |
| 6,706,043 B2 | 3/2004 | Steiner et al. |
| 6,709,458 B2 | 3/2004 | Michelson |
| 6,712,852 B1 | 3/2004 | Chung et al. |
| 6,716,245 B2 | 4/2004 | Pasquet et al. |
| 6,716,247 B2 | 4/2004 | Michelson |
| 6,719,794 B2 | 4/2004 | Gerber et al. |
| 6,730,127 B2 | 5/2004 | Michelson |
| 6,733,531 B1 | 5/2004 | Trieu |
| 6,743,256 B2 | 6/2004 | Mason |
| 6,749,636 B2 | 6/2004 | Michelson |
| 6,767,366 B2 | 7/2004 | Lee et al. |
| 6,770,096 B2 | 8/2004 | Bolger et al. |
| 6,776,798 B2 | 8/2004 | Camino et al. |
| 6,793,658 B2 | 9/2004 | LeHuec et al. |
| 6,793,679 B2 | 9/2004 | Michelson |
| 6,800,093 B2 | 10/2004 | Nicholson et al. |
| 6,808,537 B2 | 10/2004 | Michelson |
| 6,808,538 B2 | 10/2004 | Paponneau |
| 6,814,756 B1 | 11/2004 | Michelson |
| 6,830,589 B2 | 12/2004 | Erickson |
| 6,843,804 B2 | 1/2005 | Bryan |
| 6,843,805 B2 | 1/2005 | Webb et al. |
| 6,849,093 B2 | 2/2005 | Michelson |
| 6,852,126 B2 | 2/2005 | Ahlgren |
| 6,884,242 B2 | 4/2005 | LeHuec et al. |
| 6,890,355 B2 | 5/2005 | Michelson |
| 6,899,714 B2 | 5/2005 | Vaughan |
| 6,899,734 B2 | 5/2005 | Castro et al. |
| 6,926,737 B2 | 8/2005 | Jackson |
| 6,929,662 B1 | 8/2005 | Messerli et al. |
| 6,962,606 B2 | 11/2005 | Michelson |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,974,480 B2 | 12/2005 | Messerli et al. |
| 6,979,353 B2 | 12/2005 | Bresina |
| 6,984,234 B2 | 1/2006 | Bray |
| 6,987,136 B2 | 1/2006 | Erbe et al. |
| 6,989,012 B2 | 1/2006 | LeHuec et al. |
| 6,989,031 B2 | 1/2006 | Michelson |
| 7,008,453 B1 | 3/2006 | Michelson |
| 7,014,659 B2 | 3/2006 | Boyer, II et al. |
| 7,033,394 B2 | 4/2006 | Michelson |
| 7,041,135 B2 | 5/2006 | Michelson |
| 7,044,972 B2 | 5/2006 | Mathys, Jr. et al. |
| 7,077,864 B2 | 7/2006 | Byrd, III et al. |
| 7,087,056 B2 | 8/2006 | Vaughan |
| 7,112,222 B2 | 9/2006 | Fraser et al. |
| 7,118,598 B2 | 10/2006 | Michelson |
| 7,135,024 B2 | 11/2006 | Cook et al. |
| 7,135,043 B2 | 11/2006 | Nakahara et al. |
| 7,137,997 B2 | 11/2006 | Paul |
| 7,141,068 B2 | 11/2006 | Ross et al. |
| 7,163,560 B2 | 1/2007 | Mason |
| 7,163,561 B2 | 1/2007 | Michelson |
| 7,172,627 B2 | 2/2007 | Fiere et al. |
| 7,192,447 B2 | 3/2007 | Rhoda |
| 7,223,292 B2 | 5/2007 | Messerli et al. |
| 7,226,480 B2 | 6/2007 | Thalgott |
| 7,229,441 B2 | 6/2007 | Trieu et al. |
| 7,229,447 B1 | 6/2007 | Biel |
| 7,232,464 B2 | 6/2007 | Mathieu et al. |
| 7,238,203 B2 | 7/2007 | Bagga et al. |
| 7,252,673 B2 | 8/2007 | Lim |
| 7,320,708 B1 | 1/2008 | Bernstein |
| 7,326,200 B2 | 2/2008 | Trieu et al. |
| 7,326,248 B2 | 2/2008 | Michelson |
| 7,331,996 B2 | 2/2008 | Sato et al. |
| 7,332,983 B2 | 2/2008 | Larson |
| 7,338,525 B2 | 3/2008 | Ferree |
| 7,341,587 B2 | 3/2008 | Molz, IV et al. |
| 7,344,539 B2 | 3/2008 | Serhan et al. |
| 7,354,452 B2 | 4/2008 | Foley |
| 7,364,589 B2 | 4/2008 | Eisermann |
| 7,435,262 B2 | 10/2008 | Michelson |
| 7,442,209 B2 | 10/2008 | Michelson |
| 7,455,692 B2 | 11/2008 | Michelson |
| 7,540,882 B2 | 6/2009 | Michelson |
| 7,608,107 B2 | 10/2009 | Michelson |
| 7,611,536 B2 | 11/2009 | Michelson |
| 7,611,538 B2 | 11/2009 | Belliard et al. |
| 7,618,456 B2 | 11/2009 | Mathieu et al. |
| 7,621,957 B2 | 11/2009 | Errico et al. |
| 7,625,375 B2 | 12/2009 | Garden et al. |
| 7,637,951 B2 | 12/2009 | Michelson |
| 7,637,954 B2 | 12/2009 | Michelson |
| 7,815,681 B2 | 10/2010 | Ferguson |
| 2002/0099443 A1 | 7/2002 | Messerli et al. |
| 2002/0111680 A1 | 8/2002 | Michelson |
| 2002/0143400 A1 | 10/2002 | Biscup |
| 2002/0193880 A1 | 12/2002 | Fraser |
| 2002/0198598 A1 | 12/2002 | Pepper |
| 2003/0004575 A1 | 1/2003 | Erickson |
| 2003/0023312 A1 | 1/2003 | Thalgott |
| 2003/0028249 A1 | 2/2003 | Baccelli et al. |
| 2003/0083746 A1 | 5/2003 | Kuslich |
| 2003/0083747 A1 | 5/2003 | Winterbottom et al. |

| | | | | | | |
|---|---|---|---|---|---|---|
| 2003/0125739 A1 | 7/2003 | Bagga et al. | | 2006/0206208 A1 | 9/2006 | Michelson |
| 2003/0187441 A1 | 10/2003 | Bolger et al. | | 2006/0253201 A1 | 11/2006 | McLuen |
| 2003/0195632 A1 | 10/2003 | Foley et al. | | 2007/0032871 A1 | 2/2007 | Michelson |
| 2003/0199980 A1 | 10/2003 | Siedler | | 2007/0055376 A1 | 3/2007 | Michelson |
| 2004/0059419 A1 | 3/2004 | Michelson | | 2007/0106384 A1 | 5/2007 | Bray et al. |
| 2004/0210226 A1 | 10/2004 | Trieu | | 2007/0106388 A1 | 5/2007 | Michelson |
| 2004/0210310 A1 | 10/2004 | Trieu | | 2007/0208423 A1 | 9/2007 | Messerli et al. |
| 2004/0210313 A1 | 10/2004 | Michelson | | 2007/0219635 A1 | 9/2007 | Mathieu et al. |
| 2005/0065608 A1 | 3/2005 | Michelson | | 2007/0250167 A1 | 10/2007 | Bray et al. |
| 2005/0085910 A1 | 4/2005 | Sweeney | | 2007/0270965 A1 | 11/2007 | Ferguson |
| 2005/0085913 A1 | 4/2005 | Fraser et al. | | 2007/0276375 A1 | 11/2007 | Rapp |
| 2005/0113922 A1 | 5/2005 | Brazanor | | 2007/0293948 A1 | 12/2007 | Bagga et al. |
| 2005/0119751 A1 | 6/2005 | Lawson | | 2008/0021480 A1 | 1/2008 | Chin et al. |
| 2005/0125029 A1 | 6/2005 | Bernard et al. | | 2008/0051890 A1 | 2/2008 | Waugh et al. |
| 2005/0171606 A1 | 8/2005 | Michelson | | 2008/0161855 A1 | 7/2008 | Serhan et al. |
| 2005/0171607 A1 | 8/2005 | Michelson | | 2008/0161925 A1 | 7/2008 | Brittan et al. |
| 2005/0240268 A1 | 10/2005 | Messerli et al. | | 2008/0281425 A1 | 11/2008 | Thalgott et al. |
| 2005/0261774 A1 | 11/2005 | Trieu | | 2009/0012529 A1 | 1/2009 | Blain et al. |
| 2005/0267578 A1 | 12/2005 | Michelson | | 2009/0054987 A1 | 2/2009 | Chin et al. |
| 2006/0009845 A1 | 1/2006 | Chin | | 2009/0062921 A1 | 3/2009 | Michelson |
| 2006/0009846 A1 | 1/2006 | Trieu et al. | | 2009/0088849 A1 | 4/2009 | Armstrong et al. |
| 2006/0030851 A1 | 2/2006 | Bray et al. | | 2009/0105821 A1 | 4/2009 | Michelson |
| 2006/0069442 A1 | 3/2006 | Michelson | | 2009/0143862 A1 | 6/2009 | Trieu |
| 2006/0085071 A1 | 4/2006 | Lechmann et al. | | 2009/0171389 A1 | 7/2009 | Sankaran |
| 2006/0095136 A1 | 5/2006 | McLuen | | 2009/0171390 A1 | 7/2009 | Sankaran |
| 2006/0142859 A1 | 6/2006 | McLuen | | 2009/0210064 A1 | 8/2009 | Lechmann et al. |
| 2006/0167549 A1 | 7/2006 | Mathys, Jr. et al. | | 2010/0249937 A1 | 9/2010 | Blain et al. |

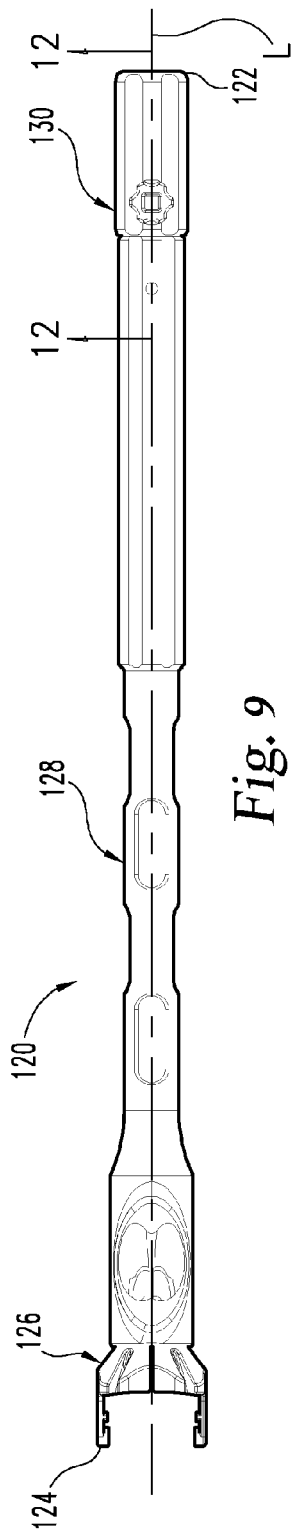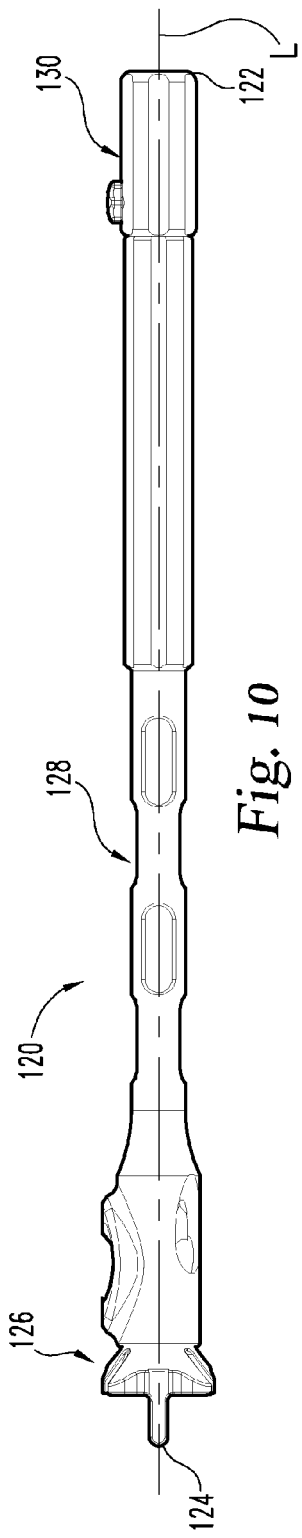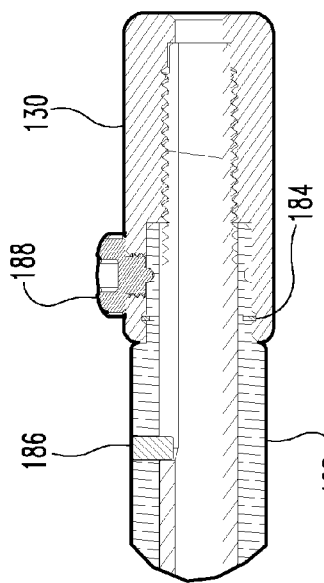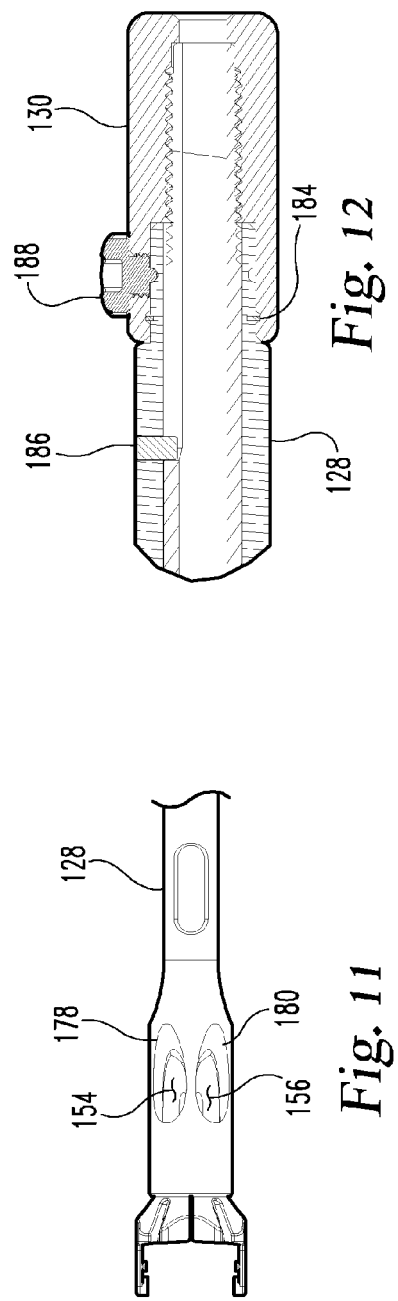
Fig. 9
Fig. 10
Fig. 12
Fig. 11

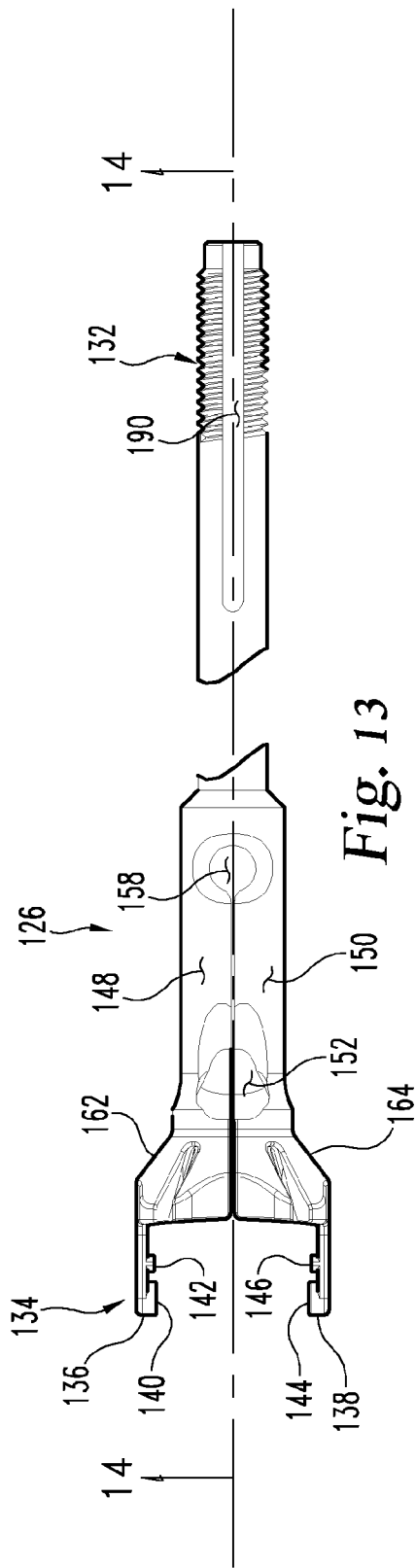
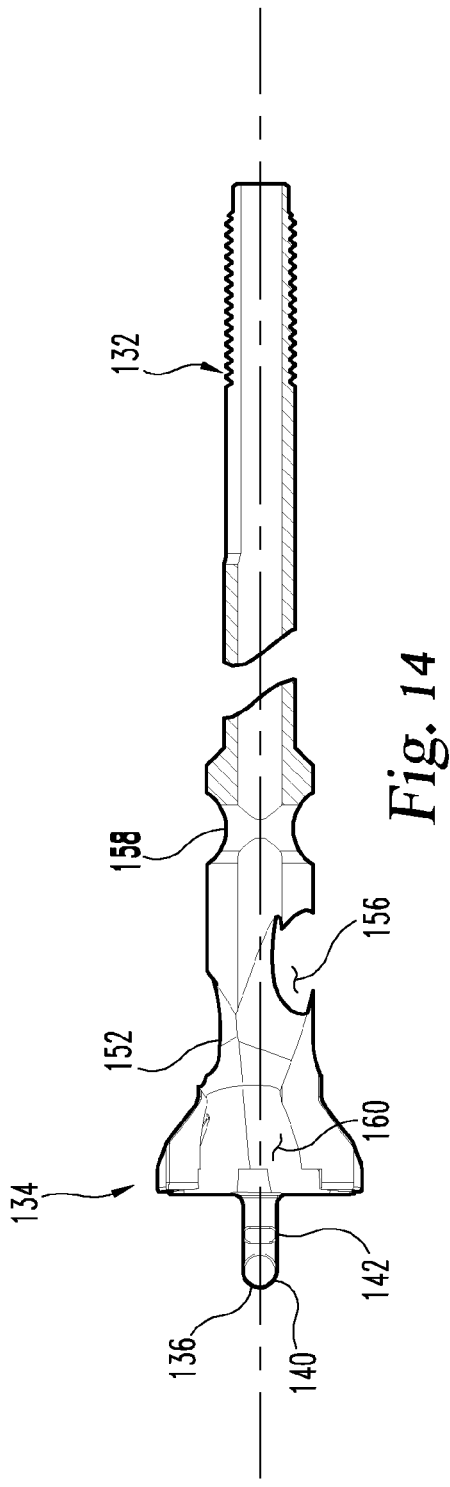

INTERBODY DEVICE AND PLATE FOR SPINAL STABILIZATION AND INSTRUMENTS FOR POSITIONING SAME

BACKGROUND

The present application relates generally to spinal stabilization involving an interbody implant device and related support plate, and to instruments and methods for inserting and positioning the device and the plate together relative to the spinal column.

Several techniques and systems have been developed for correcting and stabilizing the spine and for facilitating fusion at various levels of the spine. Some of these include positioning one or more interbody implants in a spinal disc space between adjacent vertebrae. When an implant is placed into a disc space, the channel or path that the implant took to enter the disc space provides a path for retrograde movement of the implant from the disc space. In some forms, a plate can be used to prevent retrograde movement of the implant and/or to provide additional stability to the adjacent vertebrae. If used, the plate is often positioned into engagement with the adjacent vertebrae in a separate surgical step that follows implantation of the implant. The implant can also be attached to the plate prior to implantation, although such attachment can limit adjustability of the implant and plate relative to one another to accommodate for various aspects of the spinal anatomy of the vertebrae and/or increase the length and complexity of the surgical procedure.

Thus, there remains a need for further improvements in spinal stabilization involving an interbody implant device and related support plate, and in the instruments and methods for inserting and positioning the same.

SUMMARY

Interbody implants and related support plates for spinal stabilization, as well as instruments and techniques for inserting and positioning an implant and plate together relative to the spinal column, are provided. More particularly, in one form a system includes an implant configured to be positioned in a disc space between the first and second vertebrae and a freestanding plate for engagement with the first and second vertebrae. The system also includes an insertion instrument with an engaging portion configured to releasably engage with the implant and the plate such that the implant and plate can be positioned together relative to the first and second vertebrae in a single surgical step. In one aspect, an angular orientation of the implant relative to the plate is adjustable when the implant and the plate are engaged by the instrument. In this or another aspect, the implant and plate are held in a contiguous relationship when engaged by the instrument. However, different forms and applications are also envisioned.

In one embodiment, a system for providing spinal stabilization includes an implant including a body extending from a leading end to an opposite trailing end. The body further includes a superior bone engaging surface and an opposite inferior bone engaging surface, with the superior and inferior bone engaging surfaces engaging respective endplates of upper and lower vertebrae when the implant is positioned in a spinal disc space between the upper and lower vertebrae. The system also includes a plate for engagement with the upper and lower vertebrae. The plate includes a body extending between an upper end and an opposite lower end, and the plate body includes a top surface and an opposite bottom surface facing the upper and lower vertebrae when the plate is engaged therewith. An insertion instrument includes an engaging portion configured to releasably engage with the implant and the plate such that an angular orientation of the implant relative to the plate is adjustable when the implant and the plate are engaged by the instrument.

In another embodiment, a system for providing spinal stabilization includes an implant including a body extending from a leading end to an opposite trailing end. The body further includes a superior bone engaging surface and an opposite inferior bone engaging surface, with the superior and inferior bone engaging surfaces engaging respective endplates of upper and lower vertebrae when the implant is positioned in a spinal disc space between the upper and lower vertebrae. The system also includes a plate for engagement with the upper and lower vertebrae and including a body extending between an upper end and an opposite lower end. The plate body further includes a proximal surface, an opposite distal surface, and a distal facing intermediate portion configured to cooperate with the trailing end of the implant. An insertion instrument includes an engaging portion configured to releasably engage with the implant and the plate such that the implant and the plate are held in a contiguous relationship when engaged by the instrument and the implant is displaceable from the plate upon disengagement of the instrument.

In still another embodiment, a method for providing spinal stabilization between first and second vertebrae includes providing an implant including a body extending from a leading end to an opposite trailing end, with the body also including a superior bone engaging surface and an opposite inferior bone engaging surface. The method also includes providing a plate for engagement with the first and second vertebrae. The plate includes a body extending between an upper end and an opposite lower end. Further steps of the method include engaging an insertion instrument with the implant and the plate, which includes retaining the implant and the plate in a contiguous, uncoupled arrangement; and inserting the leading end of the implant in a spinal disc space between the first and second vertebrae with the insertion instrument and advancing the implant into the disc space until a bottom surface of the plate contacts extradiscal surfaces of the first and second vertebrae. A further aspect of this embodiment includes rotating the implant relative to the plate when the insertion instrument is engaged with the implant and the plate and the implant and the plate are retained in the contiguous, uncoupled arrangement. Still, another aspect of this embodiment includes guiding at least one fastener along a corresponding guide hole through the insertion instrument and the plate into engagement with one of the vertebrae.

Other embodiments include unique methods, techniques, systems, devices, kits, assemblies, equipment, and/or apparatus for use in connection with the stabilization and support of first and second vertebrae. However, in other embodiments, different forms and applications are also envisioned.

Further embodiments, forms, features, aspects, benefits, objects and advantages of the present application will become apparent from the detailed description and figures provided herewith.

BRIEF DESCRIPTION OF THE FIGURES

FIG. 9 is a plan view of one embodiment insertion instrument configured to insert and position the interbody implant and plate of FIG. 1 relative to the spinal column.

FIG. 10 is a plan view of the insertion instrument illustrated in FIG. 9 rotated ninety degrees about its longitudinal axis.

FIG. 11 is a plan view of the distal end of the instrument illustrated in FIG. 9 rotated one hundred and eighty degrees about its longitudinal axis.

FIG. 12 is section view of the proximal end of the instrument illustrated in FIG. 9 taken along view line 12-12.

FIG. 13 is a plan view of an inner member of the instrument illustrated in FIG. 9.

FIG. 14 is a section view of the inner member illustrated in FIG. 13 taken along view line 14-14.

DESCRIPTION OF THE ILLUSTRATED EMBODIMENTS

Figure 1:
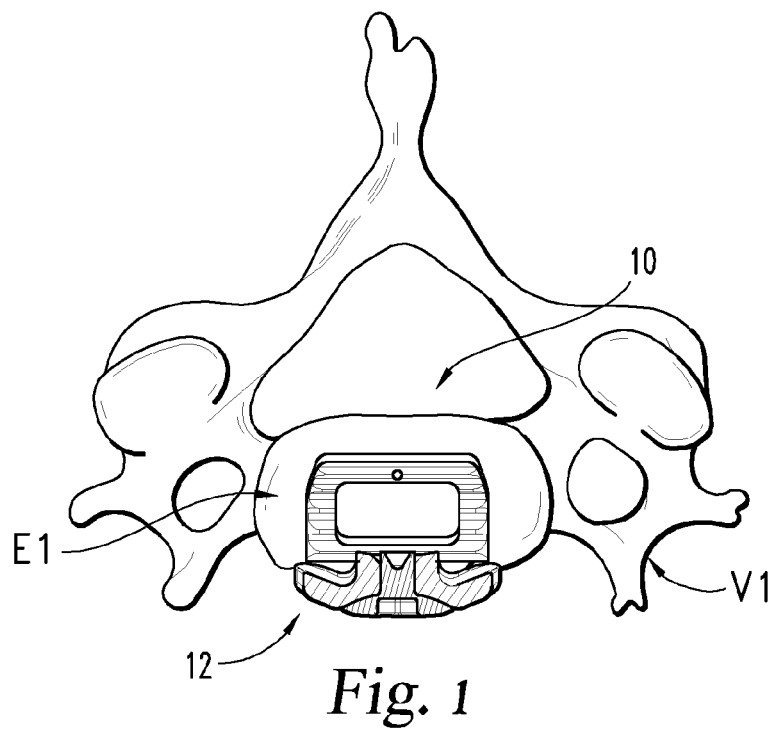
FIG. 1 is a diagrammatic plan view, with some features being shown in section, looking toward the axial plane of an endplate of a vertebral body of a spinal column with an interbody implant and plate positioned relative thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Methods, techniques, instrumentation, devices and implants are provided to restore and/or maintain a collapsed, partially collapsed, damaged, diseased, or otherwise impaired spinal disc space at a desired disc space height and adjacent endplate orientation. The instruments and implants may be used in techniques employing minimally invasive instruments and technology to access the disc space, although access in non-minimally invasive procedures is also contemplated. Access to the collapsed disc space can be uni-portal, bi-portal, or multi-portal. The instruments and implants may also be employed in a direct anterior approach to the spinal disc space, although other approaches are also contemplated, including lateral, antero-lateral, postero-lateral, oblique, and posterior approaches. Also, the surgical methods, techniques, instruments and implants may find application at all vertebral segments of the spine, including the lumbar, thoracic and cervical spinal regions.

In one aspect, interbody implants and related support plates for spinal stabilization, as well as instruments and techniques for inserting and positioning an implant and plate together relative to the spinal column, are provided. More particularly, in one form a system includes an implant configured to be positioned in a disc space between the first and second vertebrae and a freestanding plate for engagement with the first and second vertebrae. The system also includes an insertion instrument with an engaging portion configured to releasably engage with the implant and the plate such that the implant and plate can be positioned together relative to the first and second vertebrae in a single surgical step. In one aspect, an angular orientation of the implant relative to the plate is adjustable when the implant and the plate are engaged by the instrument. In this or another aspect, the implant and plate are held in a contiguous relationship when engaged by the instrument. However, different forms and applications are also envisioned.

Figure 2:
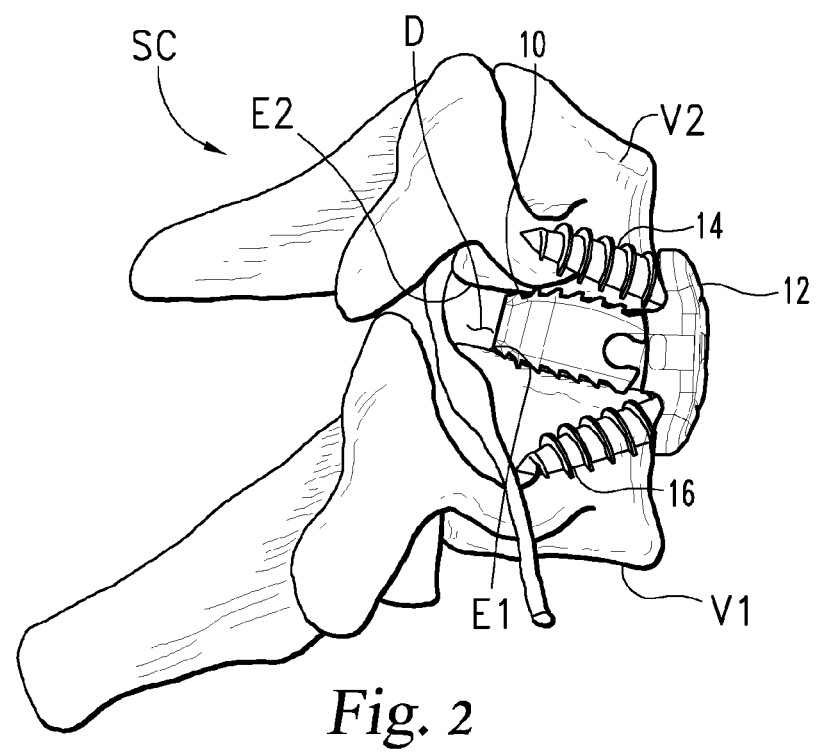
FIG. 2 is a diagrammatic elevation view looking toward the sagittal plane at a vertebral level of the spinal column including the vertebral body, interbody implant and plate of FIG. 1.

Referring now generally to FIG. 1, it illustrates a plan view, with some features being shown in section, looking caudally toward the axial plane of a vertebral body V1. As illustrated in FIGS. 1 and 2, spinal interbody implant 10 is positioned on the vertebral endplate E1 intradiscally between vertebral bodies V1, V2, and a plate 12 is secured substantially extradiscally, or outside the disc space, to vertebral bodies V1, V2 with a plurality of bone engaging fasteners, two of which are shown in the form of bone screws 14, 16. In the illustrated form, a portion of plate 12 also extends between vertebral bodies V1, V2, although forms in which plate 12 is positioned entirely extradiscally with no portion of it extending between vertebral bodies V1, V2 are also contemplated. Vertebral body V1 along with vertebral body V2 and spinal disc space D comprise a level of spinal column segment SC in the cervical region, although implantation of implant 10 and plate 12 in the thoracic and lumbar regions is also possible and contemplated, as indicated above. Implant 10 is positioned in disc space D between vertebral bodies V1 and V2 so that when it is in its implanted orientation it contacts endplates E1 and E2. In the illustrated form, plate 12 is positioned so that it lies along the anterior facing surfaces of vertebral bodies V1, V2, although positioning of plate 12 along alternatively facing surfaces of vertebral bodies V1, V2 depending on the orientation of implant 10 to vertebral bodies V1, V2 is also contemplated. Similarly, in the illustrated form vertebral bodies V1, V2 are accessed from an anterior approach, although lateral, antero-lateral, postero-lateral, oblique, and posterior approaches are also possible. Further, as illustrated, implant 10 and plate 12 are generally positioned adjacent to and in abutting engagement with one another, although it should be appreciated that movement of implant 10 away from plate 12 is possible since implant 10 and plate 12 are not physically attached or otherwise coupled to one another as will be discussed in greater detail below.

Figure 3:
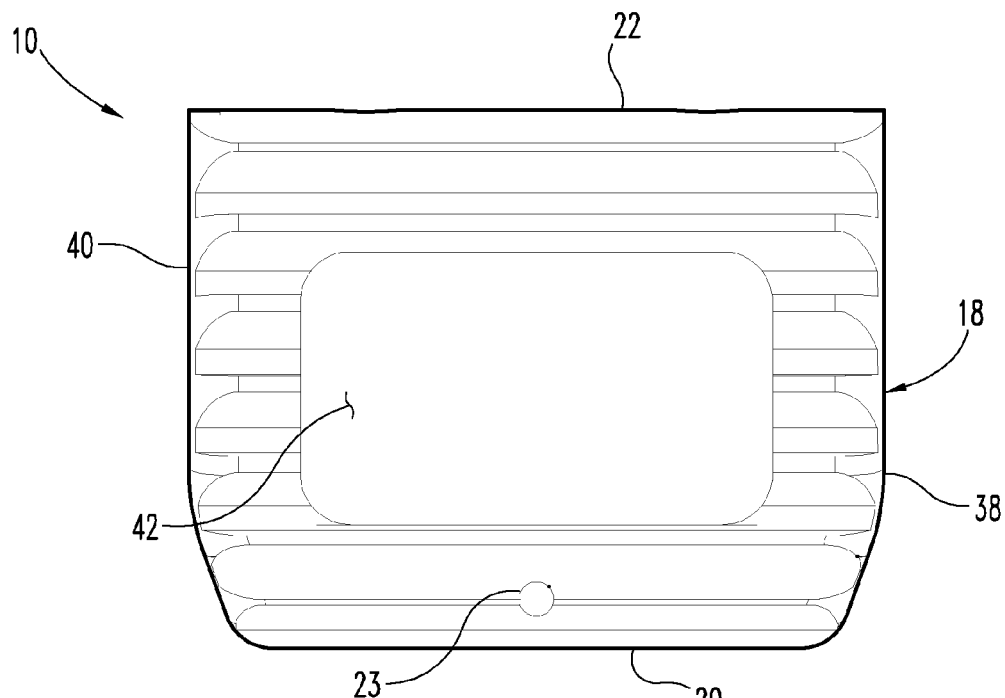
FIG. 3 is a top, plan view of the interbody implant illustrated in FIG. 1.
Figure 4:
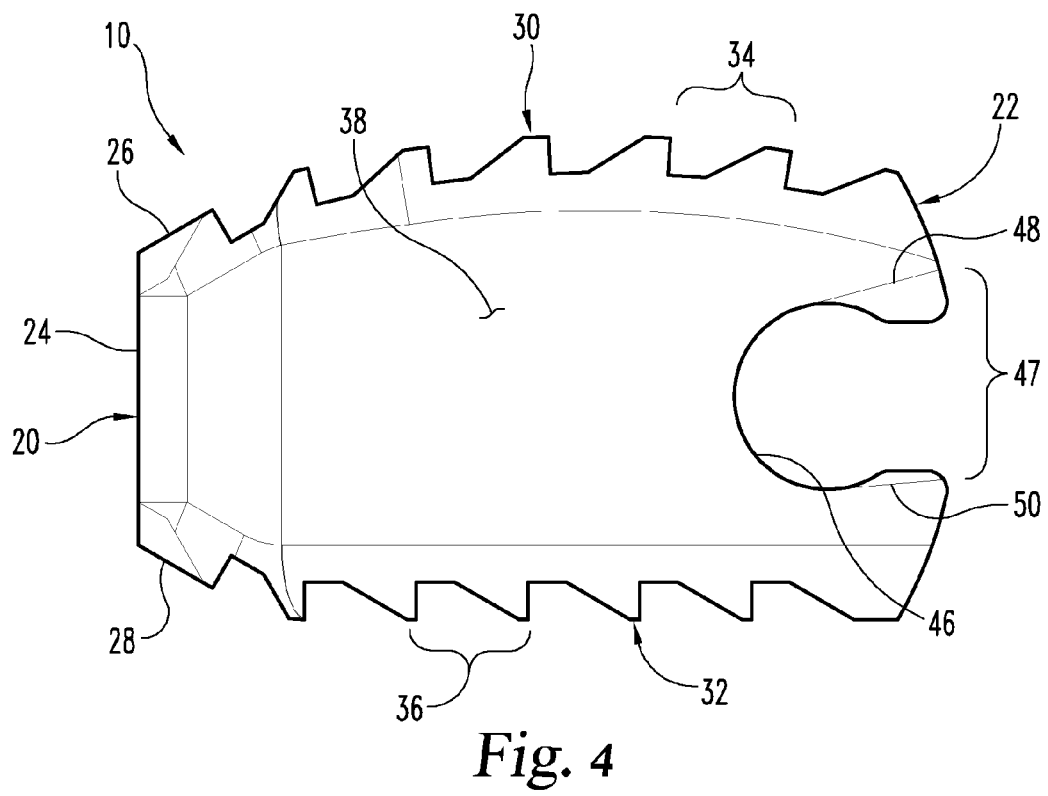
FIG. 4 is a side, plan view of the interbody implant illustrated in FIG. 1.
Figure 5:
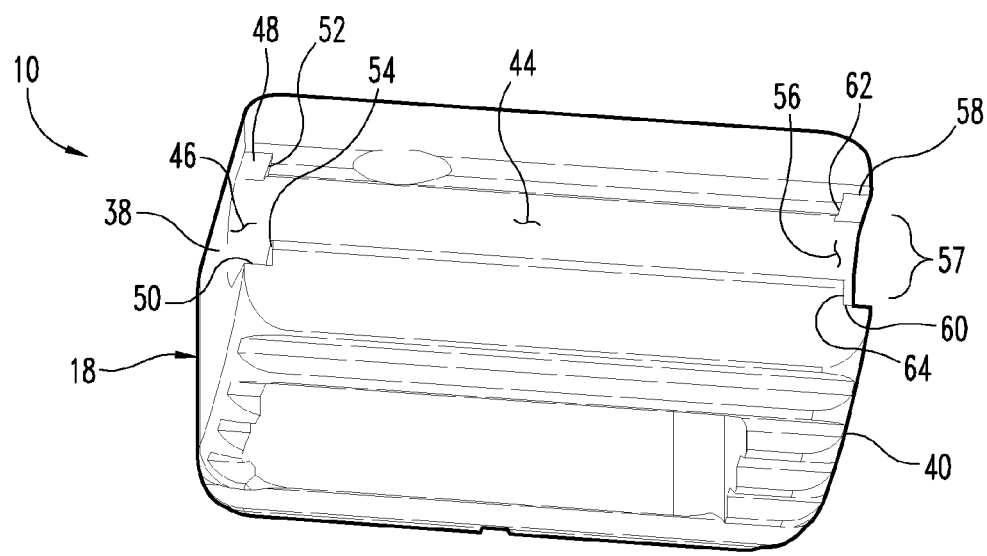
FIG. 5 is a perspective view of the interbody implant illustrated in FIG. 1.

Referring now generally to FIGS. 3-5, implant 10 includes a body 18 sized to fit within the disc space D between adjacent vertebral bodies V1, V2. Body 18 extends from a leading end 20 to an opposite trailing end 22. In the illustrated form, leading end 20 generally includes a planar surface 24 positioned between angled surfaces 26, 28 which can facilitate insertion of implant 10 into disc space D and/or distraction of vertebral bodies V1, V2. In other non-illustrated forms, leading end 20 can include a convexly rounded nose to facilitate insertion into disc space D and distraction of vertebral bodies V1, V2. As illustrated in FIG. 3 for example, body 18 also includes a receptacle 23 in which a radiographic marker can be positioned to facilitate image-guided placement of implant 10 between vertebral bodies V1, V2.

Body 18 also includes superior and inferior bone engaging surfaces 30, 32 with ridges 34, 36 (only a few of which are referenced to preserve clarity) to enhance engagement with the vertebral end plates E1, E2. In other forms, superior and inferior bone engaging surfaces 30, 32 can be provided with threads, grooves, teeth knurling or other surface roughening, just to provide a few possibilities, to enhance engagement with vertebral endplates E1, E2. In the illustrated form, bone engaging surface 30 includes a generally convex configuration between leading end 20 and trailing end 22, while bone engaging surface 32 includes a generally planar or straight configuration between leading end 20 and trailing end 22. In other forms, it should be appreciated that bone engaging surface 30 could also be planar and that bone engaging surface 32 could also be convexly curved. Still, other variations in the configurations of bone engaging surfaces 30, 32 between leading end 20 and trailing end 22 are possible. Further, bone engaging surfaces 30, 32 are generally configured such that implant 10 is received between and in contact with at least a portion of endplates E1, E2 along at least a portion of body 18. Body 18 also includes opposite side walls 38, 40 extending from leading 20 to trailing end 22, and also extending from bone engaging surface 30 to bone engaging surface 32. Side walls 38, 40 can be parallel to one another, or tapered relative to one another to converge or diverge toward the leading end 20. Side walls 38, 40 can be planar, concave or convex from leading end 20 to trailing end 22, concave or convex from bone engaging surface 30 to bone engaging surface 32, or combinations thereof.

Body 18 also includes a cavity 42 that opens through bone engaging surfaces 30, 32 to facilitate bone growth through body 18, although forms where cavity 42 is not present are also possible. In other non-illustrated forms, it is contemplated that body 18 could also include one or more openings extending through side walls 38, 40 and/or leading and trailing ends 20, 22 and into communication with cavity 42. In addition, while not illustrated, it should be appreciated that one or more biocompatible materials which, for example, provide a therapeutic effect or enhance bone growth through implant 10 can be positioned in cavity 42. Examples of such biocompatible materials may include calcium phosphate, hyrdroxyapatite-tricalcium phosphate (HA-TCP) compounds, bioactive glasses, calcium sulfate bone void fillers, collagen, fibrin, albumin, karatin, silk, elastin, demineralized bone matrix, particulate bone, mysenchymal stem cells, hormones, growth factors such as transforming growth factor beta (TGFb) proteins, bone morphogenic proteins (including BMP and BMP2), or platelet derived growth factors, just to provide a few possibilities. In one aspect, the biocompatible material(s) may, when included, extend slightly above and below bone engaging surfaces 30, 32, respectively, to facilitate compressive loading by the adjacent vertebral bodies onto and through the biocompatible material(s).

As illustrated in FIG. 4 for example, trailing end 22 of implant 10 is generally convexly curved between bone engaging surfaces 30, 32. In addition, trailing end 22 also includes an elongate slot 44 that is positioned between bone engaging surfaces 30, 32 and extends between side walls 38, 40, although in other forms it should be appreciated that trailing end 22 can be provided without elongate slot 44. Body 18 also includes a first receptacle 46 formed in side wall 38 and generally including a circular arrangement configured to receive a correspondingly configured portion of an insertion instrument, further details of which will be provided below. Body 18 also includes a notch or groove 47 formed in side wall 38. Groove 47 includes upper and lower surfaces 48, 50 and lateral facing surfaces 52, 54, and extends through trailing end 22 into communication with first receptacle 46. In the illustrated form, upper and lower surfaces 48, 50 are generally arranged in an oblique orientation relative to one another, although other forms are contemplated. Body 18 also includes a second receptacle 56 formed in side wall 40 and generally including a circular arrangement configured to receive a correspondingly configured portion of an insertion instrument, further details of which will be provided below. Body 18 also includes a notch or groove 57 formed in side wall 40. Groove 57 includes upper and lower surfaces 58, 60 and lateral facing surfaces 62, 64, and extends through trailing end 22 into communication with second receptacle 56. In the illustrated form, upper and lower surfaces 58, 60 are generally arranged in an oblique orientation relative to one another, although other forms are contemplated.

Figure 4A:
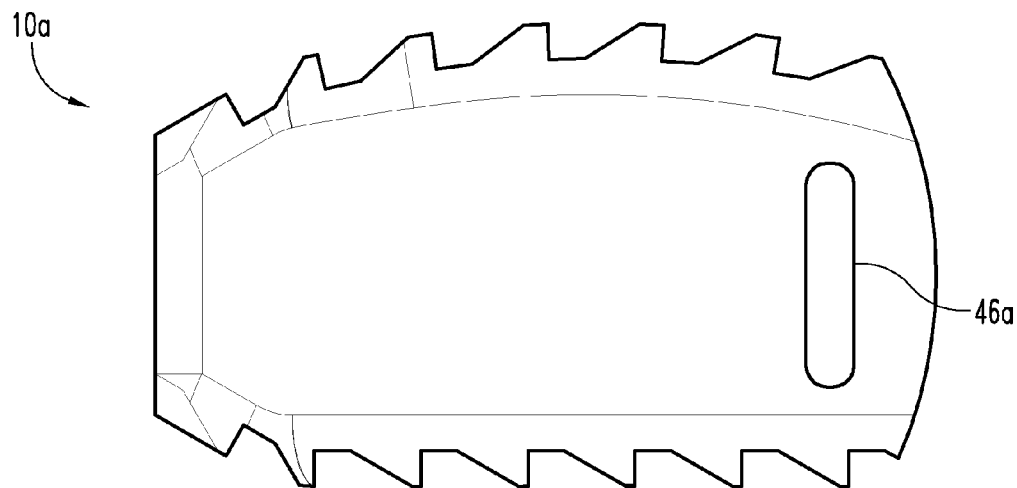
FIGS. 4A and 4B are side, plan views of alternative embodiment interbody implants.
Figure 4B:
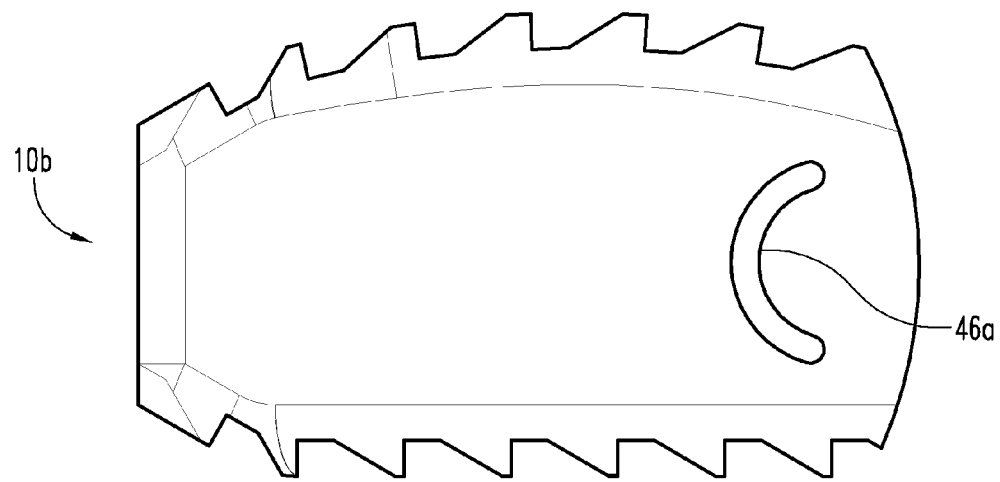

While not previously discussed, it should be appreciated that the generally circular arrangement of receptacles 46, 56 which allows receipt of a correspondingly configured portion of the insertion instrument allows an angular orientation of implant 10 relative to plate 12 to be adjusted when implant 10 and plate 12 are engaged by the insertion instrument, further details of which will be provided below. However, it should be appreciated that other configurations of implant 10 are possible for allowing the angular orientation of implant 10 relative to plate 12 to be adjusted when implant 10 and plate 12 are engaged by the insertion instrument. For example, with reference to FIG. 4A, elongate slot 44 and grooves 47, 57 have been omitted from alternative embodiment implant 10a. In addition, receptacle 46a is generally configured as an elongated slot configured to receive a round feature of the insertion instrument in order to hold implant 10a with the instrument while also allowing adjustment of the angular orientation of implant 10a relative to plate 12 and the insertion instrument when implant 10a and plate 12 are engaged by the insertion instrument. As another example, FIG. 4B illustrates another alternative embodiment implant 10b from which elongate slot 44 and grooves 47, 57 have been omitted. Implant 10b includes a receptacle 46b in the form of an arcuately shaped slot configured to receive a round feature of the insertion instrument in order to hold implant 10b with the instrument while also allowing adjustment of the angular orientation of implant 10b relative to plate 12 and the insertion instrument when implant 10b and plate 12 are engaged by the insertion instrument. While not shown in FIGS. 4A and 4B, it should be appreciated that the receptacles positioned opposite of receptacles 46a, 46b are configured the same as receptacles 46a, 46b. In addition, it should also be appreciated that other than the differences described above, implants 10a, 10b will generally be configured the same as implant 10.

Figure 6:
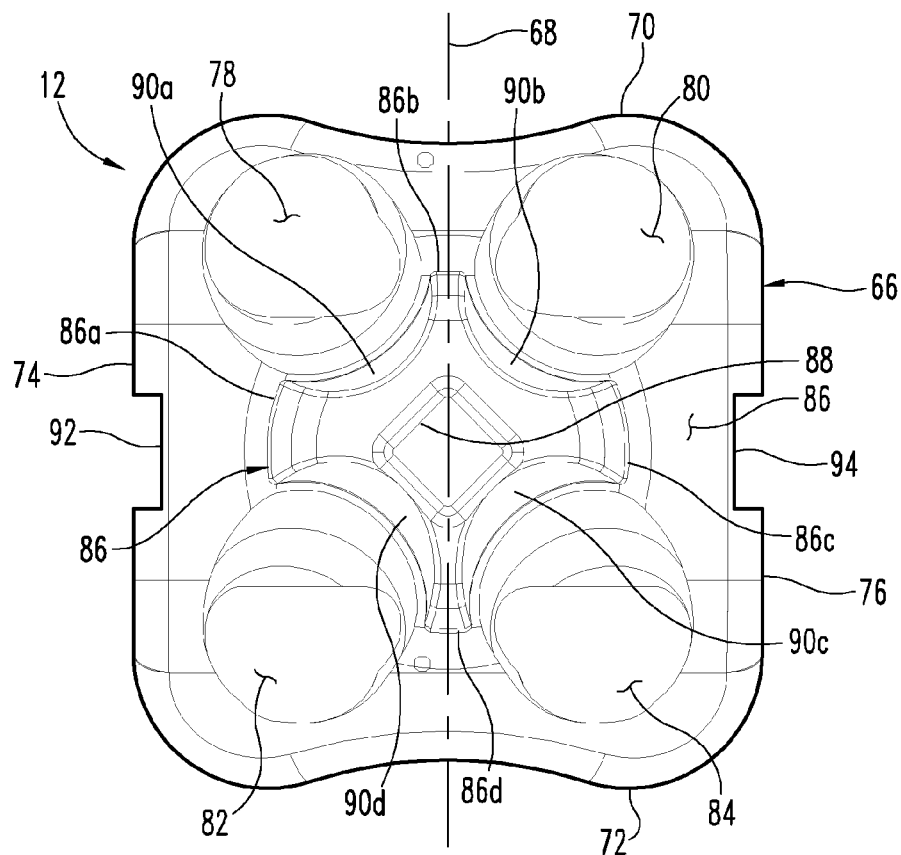
FIG. 6 is a front, plan view of the plate illustrated in FIG. 1.
Figure 7:
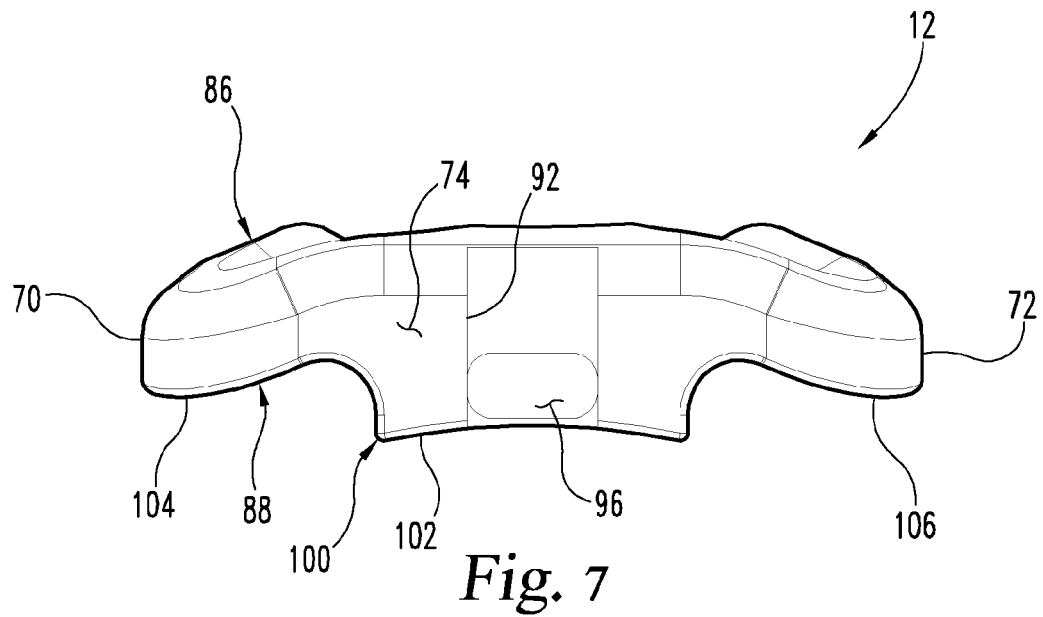
FIGS. 7 and 8 are opposite, side plan views of the plate illustrated in FIG. 1.
Figure 8:
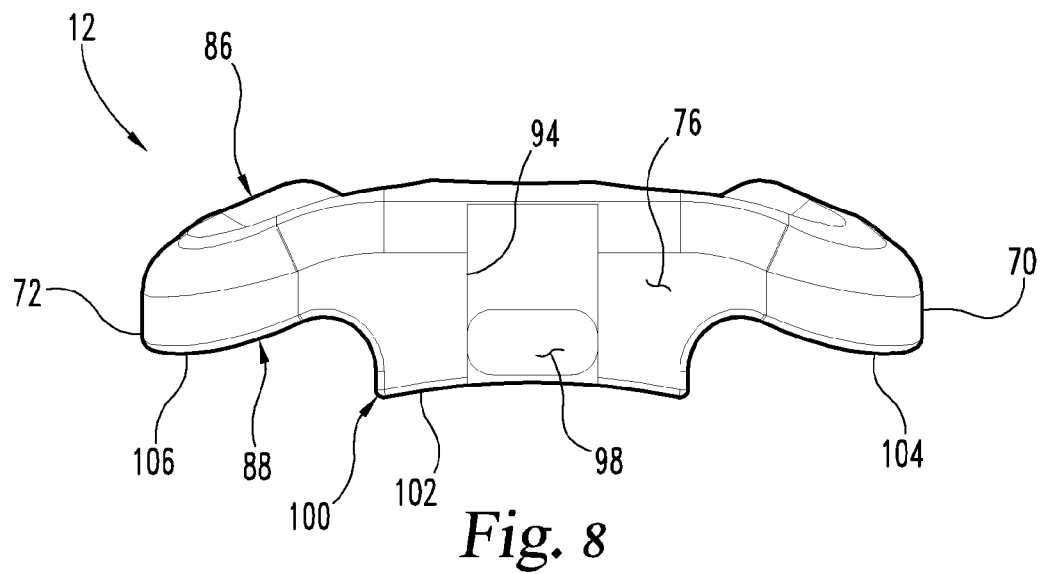
Figure 15:
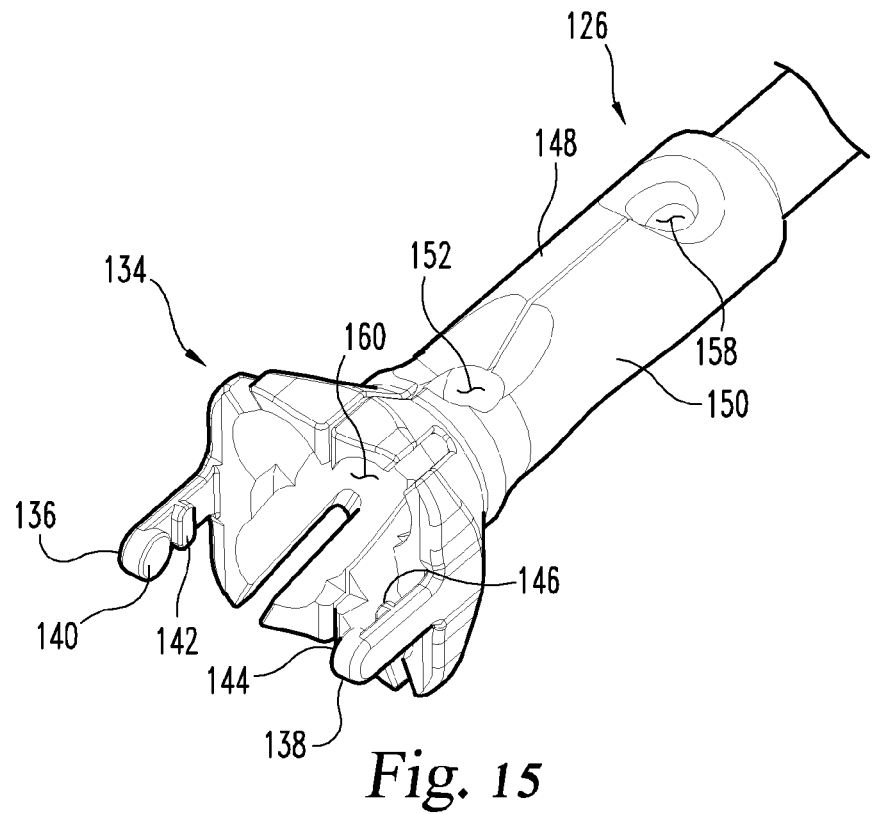
FIG. 15 is a perspective view of the distal end of the inner member illustrated in FIG. 13.

Further details regarding plate 12 are shown in FIGS. 6-8. Plate 12 includes a body 66 that extends along a central axis 68 that is oriented to extend generally along the central axis of the spinal column SC and from vertebral body V1 to vertebral body V2 when plate 12 is implanted. In the illustrated form, body 66 generally includes a substantially square configuration, although forms in which body 66 is elongated along central axis 68 and includes a rectangular, oval or elliptical shape, just to provide a few examples, are also contemplated. Body 66 includes an upper or cephalad end 70 and an opposite lower or caudal end 72, and opposite side surfaces 74, 76 that extend between ends 70, 72. Body 66 also includes superior bone screw holes 78, 80 adjacent upper end 70 and inferior bone screw holes 82, 84 adjacent lower end 72. Bone screw holes 78, 80 and 82, 84 extend through and open at top surface 86 and bottom surface 88 of body 66, and are generally arranged to allow bone screws to extend obliquely through and away from body 66. More particularly, bone screw holes 78, 80 are generally arranged to allow bone screws extending therethrough to extend obliquely to plate 12 in a lateral, cephalad direction, while bone screw holes 82, 84 are generally arranged to allow bone screws extending therethrough to extend obliquely to plate 12 in a lateral, caudal direction. Among other things, the orientation of bone screw holes 78, 80 and 82, 84 in this arrangement allows the use of relatively longer bone screws, resulting in better engagement and purchase with the adjacent vertebral bodies. Further, in this arrangement, the trajectories of bone screw holes 78, 80 and 82, 84 extend toward a common location above plate 12 such that the operating space necessary for inserting screws through plate 12 is reduced, thereby minimizing the impact to the surrounding patient anatomy. In other non-illustrated forms, it should be appreciated that plate 12 can be provided with one bone screw hole or more than two bone screw holes adjacent each of upper end 70 and lower end 72.

Body 66 also includes a retaining element 86 which can be secured to body 66 with a threaded shaft, clip or other configuration that allows retaining element 86 to rotate while attached to body 66. Retaining element 86 includes a cross-like configuration including ends 86a-d and a central driving tool receptacle 88. For the sake of clarity, it should be appreciated that retaining element 86 has been omitted from body 66 in FIGS. 7-8. The retaining element 86 also includes concavely curved sidewall portions 90a-b that can be aligned simultaneously with the respective adjacent bone screw hole 78, 80, 82, 84 to allow insertion of a bone screw and its proximal head into the adjacent bone screw hole 78, 80, 82, 84. When the bone screw heads are seated in bone screw holes 78, 80, 82, 84, retaining element 86 can be rotated so that ends 86a-d overlap the respective bone screw hole 78, 80, 82, 84 and block or contact the bone screw head to prevent bone screw back-out from bone screw holes 78, 80, 82, 84. It should also be appreciated that other shapes and designs of retaining element 86 are possible for preventing bone screw back-out from screw holes 78, 80, 82, 84. For example, in one non-illustrated form, retaining element 86 can be in the form of a threaded fastener which is engaged with plate 12 after it is attached to vertebral bodies V1, V2 such that at least a portion of an enlarged head of the threaded fastener extends over screw holes 78, 80, 82, 84.

Body 66 of plate 12 also includes grooves 92, 94 that extend into side surfaces 74, 76 and from top surface 86 to bottom surface 88. As illustrated in FIG. 7, groove 92 includes a receptacle 96 that generally has a racetrack shaped configuration. More particularly, receptacle 96 includes parallel sides between which extend arcuate or rounded end portions. As illustrated in FIG. 8, groove 94 includes a receptacle 98 that also generally has a racetrack shaped configuration. In other non-illustrated forms, it should be appreciated that other configurations, including oval or polygonal to provide a few possibilities, are also contemplated. Receptacles 96, 98 are configured to receive correspondingly configured portions of an insertion instrument, further details of which will be provided below.

In addition, body 66 also includes an intermediate portion 100 that includes a concavely shaped surface 102 facing away from top surface 86. Surface 102 is generally configured to cooperate with trailing end 22 of implant 10 when implant 10 and plate 12 are positioned adjacent to one another. Intermediate portion 100 extends away from top surface 86 such that surface 102 is offset away from top surface 86 relative to upper and lower portions 104, 106 of bottom surface 88. Similarly, as illustrated in FIG. 2 for example, this arrangement results in surface 102 and at least a portion of intermediate portion 100 being positioned in disc space D between vertebral bodies V1, V2 when upper and lower portions 104, 106 of bottom surface 88 contact vertebral bodies V1, V2 and plate 12 is engaged with vertebral bodies V1, V2. In other non-illustrated forms however, it should be appreciated that surface 102 can be aligned with upper and lower portions 104, 106 of bottom surface 88 or offset toward top surface 86 relative to upper and lower portions 104, 106 of bottom surface 88 such that no portion of plate 12 extends into disc space D when it is engaged with vertebral bodies V1, V2. In other non-illustrated forms, surface 102 can be flat or include a convex shape that is configured to cooperate with implant 10 having a concave trailing end 22.

Referring now generally to FIGS. 9-17, further details regarding an insertion instrument 120 configured to engage with implant 10 and plate 12 and position implant 10 and plate 12 relative to vertebral bodies V1, V2 will be provided. Instrument 120 extends along longitudinal axis L from proximal end 122 to distal end 124 and includes an inner member 126, outer member 128 and a drive member 130. Inner member 126 extends between a threaded proximal portion 132 and a distal engaging portion 134. Distal engaging portion 134 is bifurcated into portions 148, 150 which surround a hollow interior 160 and from which tines 136, 138 extend. Portions 148, 150 also include tapered surfaces 162, 164 adjacent the proximal ends of tines 136, 138, and are pivotable about passage 158 such that tines 136, 138 can be moved relative to one another to facilitate engagement and disengagement of instrument 120 with implant 10 and plate 12. While not illustrated, it should be appreciated that a spring or other resiliently elastic material, such as a rubber plug, can be positioned in passage 158 such that tines 136, 138 are normally biased away from one another. Tine 136 includes a distal, generally circular shaped projection 140 configured to be positioned in receptacle 46 of implant 10. Tine 136 also includes a generally racetrack shaped projection 142 proximally spaced from projection 140 and configured to be positioned in receptacle 96 of plate 12. Tine 136 is further configured to be positioned in groove 47 of implant 10 and groove 92 of plate 12 when instrument 120 is engaged with implant 10 and plate 12. Tine 138 includes a distal, generally circular shaped projection 144 configured to be positioned in receptacle 56 of implant 10. Tine 138 also includes a generally racetrack shaped projection 146 proximally spaced from projection 144 and configured to be positioned in receptacle 98 of plate 12. Tine 138 is further configured to be positioned in groove 57 of implant 10 and groove 94 of plate 12 when instrument 120 is engaged with implant 10 and plate 12. Inner member 126 also includes an opening 152 that extends obliquely to longitudinal axis L and into communication with hollow interior 160. Another set of openings 154, 156 are positioned opposite of opening 152 and extend obliquely to longitudinal axis L and into communication with hollow interior 160.

Outer member 128 extends between proximal end 170 and distal end 172 and includes a hollow interior 174 which receives inner member 126. Outer member 128 also includes an opening 176 that extends obliquely to longitudinal axis L and into communication with hollow interior 174. A ridge 177 extends along a portion of opening 176 and defines opposite portions 176a, 176b of opening 176. Another set of openings 178, 180 (FIG. 11) are positioned opposite of opening 176 and extend obliquely to longitudinal axis L and into communication with hollow interior 174. When inner member 126 is positioned in outer member 128 and instrument 120 engages with implant 10 and plate 12, opening 176 of outer member 128 generally aligns with opening 152 of inner member 126 and openings 178, 180 of outer member 128 generally align with openings 154, 156 of inner member 126. Similarly, in this arrangement, cooperation of openings 152, 176 allows placement of bone screws through instrument 120 into and through bone screw holes 82, 84 of plate 12. More particularly, portion 176a of opening 176 and opening 152 are arranged such that ridge 177 guides a bone screw to bone screw opening 82 of plate 12, while portion 176b of opening 176 and opening 152 are arranged such that ridge 177 guides a bone screw to bone screw opening 84 of plate 12. Further, cooperation of openings 154, 156 and openings 178, 180 allows placement of bone screws through instrument 120 into and through bone screw holes 78, 80 of plate 12. More particularly, openings 154 and 178 are generally arranged relative to instrument 120 to guide a bone screw to bone screw opening 80 of plate 12, while openings 156 and 180 are generally arranged relative to instrument 120 to guide a bone screw to bone screw opening 78 of plate 12. In addition, while not previously discussed, it should be appreciated that cooperation of openings 152, 176 may also facilitate engagement of receptacle 88 of retaining element 86 to facilitate rotation of retaining element 86 following placement of the bone screws, although engagement of retaining element 86 by inserting an instrument along the length of instrument 120 through hollow interior 160 is also contemplated. In addition, while not previously discussed, it should also be appreciated that the cooperation of openings 152, 176, openings 154, 178 and openings 156, 180 may also facilitate access to vertebral bodies V1, V2 with one or more instruments such as awls, drills or taps, just to provide a few possibilities, to prepare vertebral bodies V1, V2 for the bone screws.

Proximal end 170 of outer member 128 also includes an annular groove 182 within which is positioned a retaining ring 184 in order to couple outer member 128 with drive member 130 such that drive member 130 is independently rotatable relative to outer member 128. Drive member 130 includes internal threading configured to engage with threaded proximal portion 132 of inner member 126. Similarly, rotation of drive member 130 results in axial displacement of inner member 126 along longitudinal axis L relative to outer member 128. A pin 186 extends from outer member 128 into a slot 190 on inner member 126 to prevent rotation of inner member 126 relative to outer member 128. Further, a locking member 188 extends through drive member 130 and is selectively engageable with inner member 126 to prevent rotation of drive member 130 relative to inner member 126 once a desired relationship between inner member 126 and outer member 128 has been obtained. While not previously discussed, it should be appreciated that axial movement of inner member 126 along longitudinal axis L in a proximal direction relative to outer member 128 results in engagement of distal end 172 of outer member 128 with tapered surfaces 162, 164 of distal engaging portion 134 of inner member 126. As distal end 172 engages with tapered surfaces 162, 164, portions 148, 150 and tines 136, 138 are forced toward one another. Moreover, axial movement of inner member 126 along longitudinal axis L in a distal direction relative to outer member 128 disengages distal end 172 of outer member 128 from tapered surfaces 162, 164 to allow portions 148, 150 and tines 136, 138 to be moved away from one another.

Figure 18:
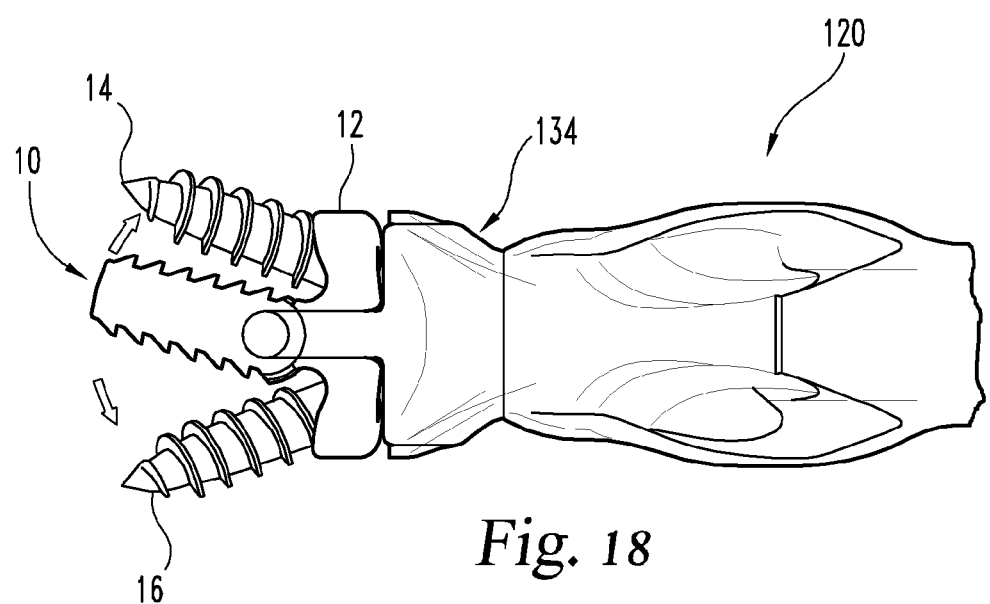
FIG. 18 is a plan view of the instrument illustrated in FIG. 9 engaged with the interbody implant and plate of FIG. 1.
Figure 16:
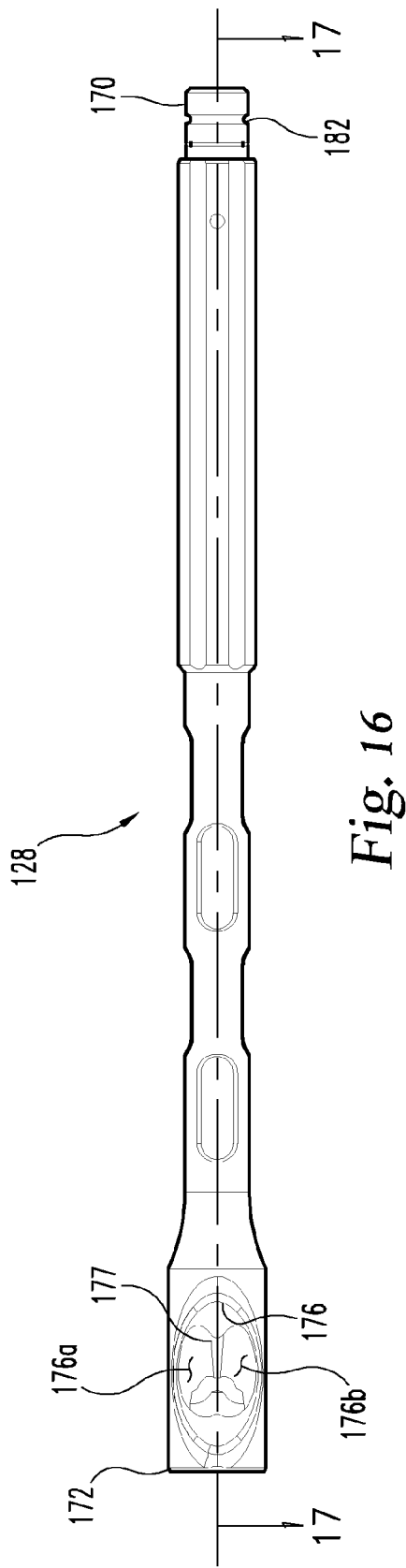
FIG. 16 is a plan view of an outer member of the instrument illustrated in FIG. 9.
Figure 17:
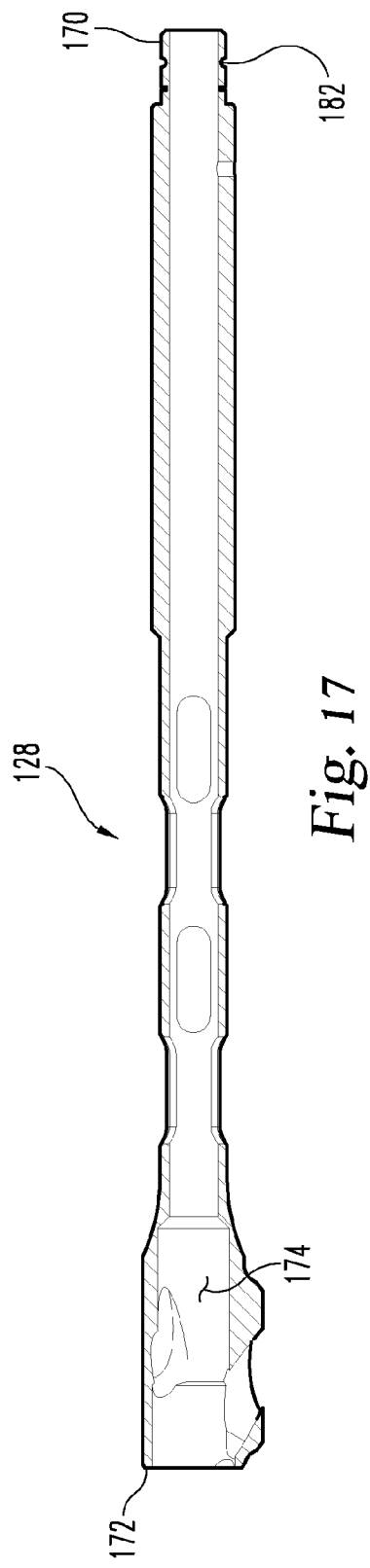
FIG. 17 is a section view of the outer member illustrated in FIG. 16 taken along view line 17-17.

As indicated above, implant 10 and plate 12 are not coupled or otherwise attached with one another. However, implant 10 and plate 12 can be positioned adjacent one another with trailing end 22 of implant 10 cooperating with surface 102 of plate 12. When implant 10 and plate 12 are positioned in this arrangement, they may each be engaged by instrument 120 as illustrated in FIG. 18 for example. More particularly, tine 136 can be positioned in groove 94 of plate 12 and in groove 57 of implant 10 with projection 140 positioned in receptacle 56 of implant 10 and projection 142 positioned in receptacle 98 of plate 10. Similarly, tine 138 can be positioned in groove 92 of plate 12 and in groove 47 of implant 10 with projection 144 positioned in receptacle 46 of implant 10 and projection 146 positioned in receptacle 96 of plate 10. Once tines 136, 183 are engaged with implant 10 and plate 12, inner member 126 can be moved proximally relative to outer member 128 to clamp implant 10 and plate 12 between tines 136, 138. Engagement of implant 10 and plate 12 with instrument 120 generally holds implant 10 and plate 12 in a contiguous relationship. More particularly, engagement of projections 140, 144 with receptacles 46, 56 of implant 10 and engagement of projections 142, 146 with receptacles 96, 98 of plate 10 prevents displacement of implant 10 from plate 12. However, once disengaged by instrument 120, implant 10 may be displaced from plate 12.

While not previously discussed, it should be appreciated that the circular configuration of receptacles 46, 56 and projections 140, 144, as well as the convex shape of trailing end 22 of implant 10 and the corresponding concave shape of surface 102 of plate 12, allow implant 10 to rotate relative to instrument 120 and plate 12 when it is engaged by instrument 120. Further, the racetrack shaped configuration of grooves 96, 98 and projections 142, 146 prevents rotation of plate 12 relative to instrument 120 when it engages plate 12. In the illustrated form, rotation of implant 10 relative to plate 12 and instrument 120 will be limited in a first direction by contact of tine 136 with upper surface 58 of groove 57 and of tine 138 with upper surface 48 of groove 47, and in a second direction by contact of tine 136 with lower surface 60 of groove 57 and of tine 138 with lower surface 50 of groove 47. Similarly, it should be appreciated that the orientation of upper and lower surfaces 48, 50 relative to one another and of upper and lower surfaces 58, 60 relative to one another can be modified to facilitate differing degrees of rotation of implant 10 relative to plate 12 when they are engaged by instrument 120. In other forms however, it is contemplated that implant 10 can be configured such that its rotation relative to plate 12 is not limited.

When engaged by instrument 120, implant 10 and plate 12 can be positioned relative to vertebral bodies V1, V2 together in a single surgical step. More particularly, leading end 20 of implant 12 can be positioned in disc space D between vertebral bodies V1, V2 and advanced into disc space D until bottom surface 88 of plate 12 contacts vertebral bodies V1, V2. As implant 10 is inserted and advanced into disc space D, it can rotate relative to plate 12 as necessary to accommodate for the orientation of vertebral bodies V1, V2 relative to disc space D. For example, when implant 10 and plate 12 are used in a curved or lordotic portion of the spinal column SC, implant 10 may extend obliquely as illustrated in FIG. 18, rather than orthogonally, to plate 12 once it is inserted in disc space D. Once implant 10 is properly positioned in disc space D and plate 12 is positioned against vertebral bodies V1, V2, bone screws can be inserted through instrument 120 to attach plate 12 to vertebral bodies V1, V2, and retaining element 86 can be rotated to position ends 86a-d over the bone screws to prevent screw back-out. While only two bone screws have bone illustrated in FIG. 18, it should be appreciated that plate 12 may be attached to vertebral bodies V1, V2 with an upper pair of screws and a lower pair of screws. After the screws have been inserted and covered by retaining element 86, instrument 120 may be disengaged from implant 10 and plate 12 and removed from the surgical site.

Figure 19:
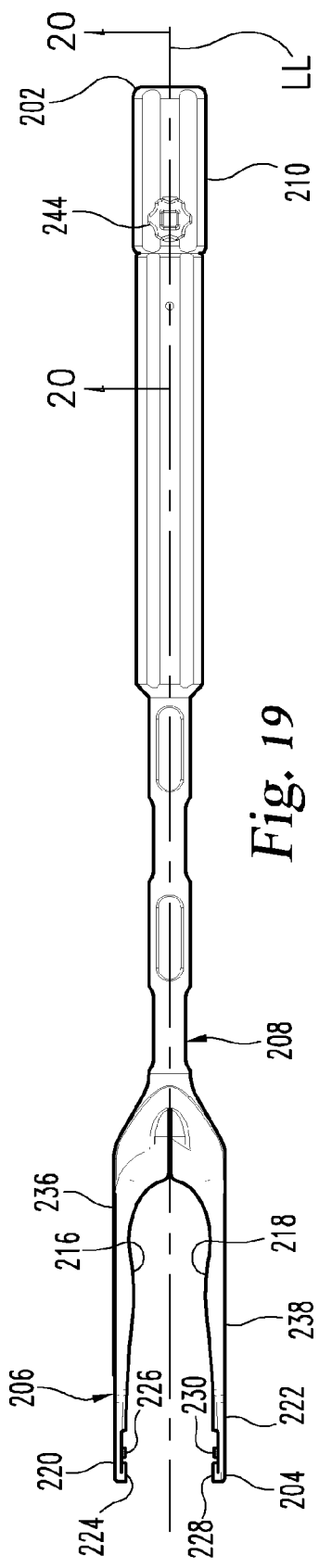
FIG. 19 is a plan view of an alternative embodiment insertion instrument configured to insert and position the interbody implant and plate of FIG. 1 relative to the spinal column.
Figure 20:
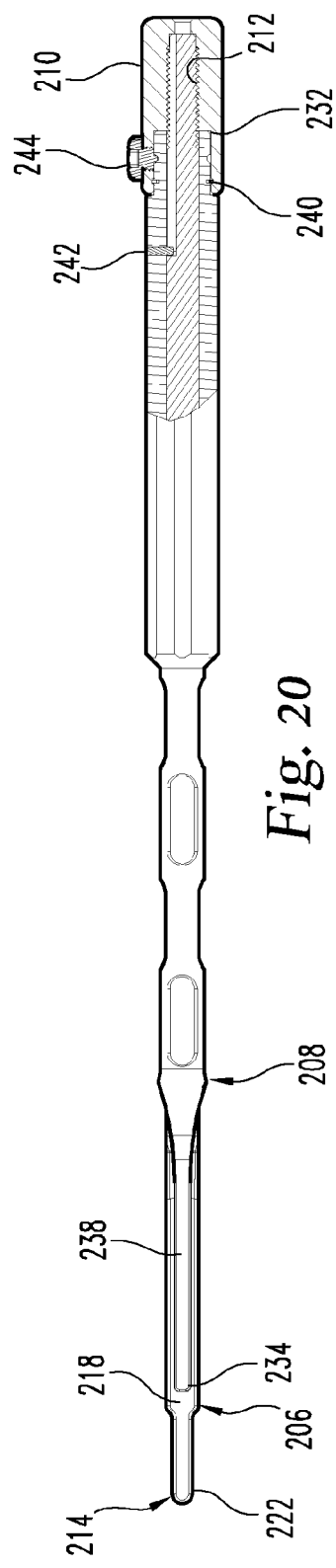
FIG. 20 is a plan view of the insertion instrument illustrated in FIG. 19 rotated ninety degrees about its longitudinal axis and with some features being shown in section along view line 20-20.

An alternative embodiment insertion instrument 200 configured to engage with implant 10 and plate 12 and position implant 10 and plate 12 relative to vertebral bodies V1, V2 is illustrated in FIGS. 19-20. Instrument 200 extends along longitudinal axis LL from proximal end 202 to distal end 204 and includes an inner member 206, outer member 208 and a drive member 210. Inner member 206 extends between a threaded proximal portion 212 and a distal engaging portion 214. Distal engaging portion 214 is bifurcated into portions 216, 218 that form tines 220, 222. Portions 216, 218 also include tapered surfaces positioned proximally of tines 220, 222 and are laterally displaceable relative to one another such that tines 220, 222 can be moved to facilitate engagement and disengagement of instrument 200 with implant 10 and plate 12. Tine 220 includes a distal, generally circular shaped projection 224 configured to be positioned in receptacle 46 of implant 10. Tine 220 also includes a generally racetrack shaped projection 226 proximally spaced from projection 224 and configured to be positioned in receptacle 96 of plate 12. Tine 220 is further configured to be positioned in groove 47 of implant 10 and groove 92 of plate 12 when instrument 200 is engaged with implant 10 and plate 12. Tine 222 includes a distal, generally circular shaped projection 228 configured to be positioned in receptacle 56 of implant 10. Tine 222 also includes a generally racetrack shaped projection 230 proximally spaced from projection 228 and configured to be positioned in receptacle 98 of plate 12. Tine 222 is further configured to be positioned in groove 57 of implant 10 and groove 94 of plate 12 when instrument 200 is engaged with implant 10 and plate 12.

Outer member 208 extends between proximal end 232 and distal end 234 and includes a hollow interior within which inner member 206 is received. Distal end 234 also includes opposing tines 236, 238 which are configured to extend along and engage with lateral surfaces of tines 220, 222. Outer member 208 also includes tapered surfaces positioned proximally of tines 236, 238 and configured to engage with the tapered surfaces of inner member 206. Proximal end 232 of outer member 208 also includes an annular groove within which is positioned a retaining ring 240 in order to couple outer member 208 with drive member 210 such that drive member 210 is independently rotatable relative to outer member 208. Drive member 210 includes internal threading configured to engage with threaded proximal portion 212 of inner member 206. Similarly, rotation of drive member 210 results in axial displacement of inner member 206 along longitudinal axis L relative to outer member 208. A pin 242 extends from outer member 208 into a slot on inner member 206 to prevent rotation of inner member 206 relative to outer member 208. Further, a locking member 244 extends through drive member 210 and is selectively engageable with inner member 206 to prevent rotation of drive member 210 relative to inner member 206 once a desired relationship between inner member 206 and outer member 208 has been obtained. While not previously discussed, it should be appreciated that axial movement of inner member 206 along longitudinal axis L in a proximal direction relative to outer member 208 results in engagement of the tapered surfaces of outer member 208 with the tapered surfaces of inner member 206 which forces tines 220, 222 toward one another. Moreover, axial movement of inner member 206 along longitudinal axis L in a distal direction relative to outer member 208 disengages the tapered surfaces of inner and outer members 206, 208 to allow portions 216, 218 and tines 220, 222 to be moved away from one another.

When implant 10 and plate 12 are positioned adjacent one another as discussed above, they may each be engaged by instrument 200. More particularly, tine 220 can be positioned in groove 94 of plate 12 and in groove 57 of implant 10 with projection 224 positioned in receptacle 56 of implant 10 and projection 226 positioned in receptacle 98 of plate 10. Similarly, tine 222 can be positioned in groove 92 of plate 12 and in groove 47 of implant 10 with projection 228 positioned in receptacle 46 of implant 10 and projection 230 positioned in receptacle 96 of plate 10. Once tines 220, 222 are engaged with implant 10 and plate 12, inner member 206 can be moved proximally relative to outer member 208 to clamp implant 10 and plate 12 between tines 220, 222. Engagement of implant 10 and plate 12 with instrument 200 generally holds implant 10 and plate 12 in a contiguous relationship. More particularly, engagement of projections 224, 228 with receptacles 46, 56 of implant 10 and engagement of projections 226, 230 with receptacles 96, 98 of plate 10 prevents displacement of implant 10 from plate 12. However, once disengaged by instrument 200, implant 10 is freely displaceable from plate 12.

While not previously discussed, it should be appreciated that the circular configuration of receptacles 46, 56 and projections 224, 228, as well as the convex shape of trailing end 22 of implant 10 and the corresponding concave shape of surface 102 of plate 12, allows implant 10 to rotate relative to instrument 200 and plate 12 when it is engaged by instrument 200. Further, the racetrack shaped configuration of grooves 96, 98 and projections 226, 230 prevents rotation of plate 12 relative to instrument 200 when it engages plate 12. In the illustrated form, rotation of implant 10 relative to plate 12 and instrument 200 will be limited in a first direction by contact of tine 220 with upper surface 58 of groove 57 and of tine 222 with upper surface 48 of groove 47, and in a second direction by contact of tine 220 with lower surface 60 of groove 57 and of tine 222 with lower surface 50 of groove 47. Similarly, it should be appreciated that the orientation of upper and lower surfaces 48, 50 relative to one another and of upper and lower surfaces 58, 60 relative to one another can be modified to facilitate differing degrees of rotation of implant 10 relative to plate 12 when they are engaged by instrument 200. In other forms however, it is contemplated that implant 10 can be configured such that its rotation relative to plate 12 is not limited. When engaged by instrument 200, implant 10 and plate 12 can be positioned relative to vertebral bodies V1, V2 together in a single surgical step, as discussed above in connection with instrument 120. Once implant 10 and plate 12 are positioned relative to vertebral bodies V1, V2, one or more instruments for preparing vertebral bodies V1, V2 to receive bone screws can be positioned between tines 220, 222 and through the bone screw holes 78, 80, 82, 84 of plate 12, followed by insertion of the bone screws through plate 12 from between tines 220, 222.

As discussed above, instruments 120, 200 can be used to engage and insert implant 10 and plate 12 which is freestanding from implant 10; i.e., plate 12 is not mechanically attached or otherwise coupled to implant 10. In this form, implant 10 and plate 12 are held adjacent to one another in a contiguous relationship by instruments 120, 200, but are otherwise freely displaceable to one another when not engaged by instruments 120, 200. Further, engagement of implant 10 and plate 12 with instruments 120, 200 allows implant 10 to be pivoted relative to plate 12, which is held stationary by instruments 120, 200, and to instruments 120, 200 so that the orientation of implant 10 relative to plate 12 can be adjusted during implantation of implant 10 and plate 12. In other non-illustrated forms, it should be appreciated that the configurations of implant 10 and plate 12 can be reversed such that plate 12 can be pivoted relative to implant 10, which is held stationary by instruments 120, 200, and to instruments 120, 200 so that the orientation of plate 12 relative to implant 10 can be adjusted during implantation of implant 10 and plate 12. In other forms, it is also contemplated that instruments 120, 200 can be used to engage and insert an implant which is coupled to a plate. Moreover, while specific designs of implant 10 and plate 12 have been illustrated and described, it should be appreciated that other designs of implant 10 and plate 12 also fall within the scope of this disclosure.

In addition, while not previously discussed, it should be appreciated that implant 10 is generally centered on plate 12 when implant 10 and plate 12 are engaged by instruments 120, 200. Similarly, in this arrangement, plate 12 will generally be centered relative to implant 10 and the corresponding disc space into which implant 10 is inserted following positioning of implant 10 and plate 12 with instruments 120, 200 without any further manipulation or adjusting of plate 12. Amongst other things, the centering of plate 12 relative to implant 10 by this arrangement results in bone screw holes 78, 80 and 82, 84 being appropriately positioned relative to the endplates of the vertebrae positioned on opposite sides of the disc space to facilitate insertion of bone screws therethrough and into engagement with the vertebrae. Similarly, in certain aspects, given the proper placement of bone screw holes 78, 80 and 82, 84 relative to the adjacent vertebrae due to the centering effect of plate 12 relative to implant 10 provided by instruments 120, 200, plate 12 can be provided with a relatively smaller length. However, in other aspects, it is contemplated that the length of plate 12 is not adjusted due to this arrangement.

In one embodiment, a system for providing stabilization to first and second vertebrae includes an implant configured to be positioned between the vertebrae and a plate configured to be positioned against and engaged with an exterior surface of each vertebra. The implant and plate can each be engaged by a single surgical instrument in an arrangement that facilitates adjustment of the orientation of the implant and plate relative to one another during implantation of the implant and plate. Further, engagement of the implant and plate by the instrument facilitates implantation of the implant and plate together in a single surgical step without eliminating adjustability of implant relative to the plate. In one aspect, the implant and plate are freestanding relative to each other (i.e., the implant and plate are not coupled to one another) and the instrument holds the implant and plate in a contiguous relationship when it is engaged therewith.

While not previously discussed, it should be appreciated that, unless otherwise described, the implants, devices, and instruments described herein may be made from any suitable biocompatible material, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities. The implants and plates can be made from the same material, or of different material. Of course, it is understood that the relative size of the components can be modified for the particular vertebra(e) to be instrumented and for the particular location or structure of the vertebrae relative to which the implant and plate will be positioned.

Further, it should also be appreciated that the implants, instruments, devices, systems, techniques and methods described herein may also be used in surgical procedures involving animals, or in demonstrations for training, education, marketing, sales and/or advertising purposes. Furthermore, the implants, instruments, devices, systems, techniques and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words/phrases such as "a", "an", "at least one", and/or "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A system for providing spinal stabilization, comprising:
an implant including a body extending from a leading end to an opposite trailing end, said body including a superior bone engaging surface and an opposite inferior bone engaging surface, said superior and inferior bone engaging surfaces engaging respective endplates of upper and lower vertebrae when said implant is positioned in a spinal disc space between the upper and lower vertebrae;
a plate for engagement with the upper and lower vertebrae, said plate including a body extending between an upper end and an opposite lower end, said plate body including a top surface and an opposite bottom surface facing the upper and lower vertebrae when said plate is engaged therewith, said plate including a plurality of holes and a retaining element rotatably disposed on an outer surface of said plate, said retaining element comprising a plurality of arms separated by gaps such that said retaining element is rotatable between a first position where said arms do not cover said plurality of holes and a second position where said arms cover said plurality of holes; and
an insertion instrument including an engaging portion configured to releasably engage with said implant and said plate, wherein an angular orientation of said implant relative to said plate is adjustable when said implant and said plate are engaged by said instrument.

2. The system of claim 1, wherein rotation of said plate relative to said instrument is limited when said implant and said plate are engaged by said insertion instrument.

3. The system of claim 2, wherein engagement of said implant and said plate with said instrument prevents displacement of said implant relative to said plate and upon disengagement of said implant and said plate from said instrument said implant is freely displaceable relative to said plate.

4. The system of claim 1, wherein said implant includes a first pair of receptacles positioned on opposite sides of said implant between said superior and inferior bone engaging surfaces and said plate includes a second pair of receptacles positioned on opposite sides of said plate between said top and bottom surfaces.

5. The system of claim 4, wherein said engaging portion of said instrument includes a pair of oppositely positioned tines, said tines each including a first projection configured to be positioned in a respective one of said first pair of receptacles and a second projection configured to be positioned in a respective one of said second pair of receptacles.

6. The system of claim 5, wherein said plate includes first and second grooves formed in said opposite sides and extending between said top and bottom surfaces, and a respective one of said second pair of receptacles is positioned in each of said first and second grooves.

7. The system of claim 6, wherein said implant includes a first notch extending from a first one of said first pair of receptacles and opening through said trailing end of said implant and a second notch extending from a second one of said first pair of receptacles and opening through said trailing end of said implant.

8. The system of claim 7, wherein said tines are positioned in respective ones of said first notch and said first groove and said second notch and said second groove when said implant and said plate are engaged by said instrument.

9. The system of claim 5, wherein said first projections of said tines include a generally cylindrical shaped configuration and said second projections of said tines include a generally racetrack shaped configuration.

10. The system of claim 5, wherein said first projections of said tines are positioned at a distal end of said instrument and said second projections of said tines are spaced proximally of said first projections.

11. The system of claim 1, wherein said plate body includes a pair of holes adjacent to said upper end that extend through said top and bottom surfaces and a second pair of holes adjacent to said lower end that extend through said top and bottom surfaces, and further comprising a first pair of bone engaging fasteners extending through said first pair of holes for engagement with the upper vertebra and a second pair of bone engaging fasteners extending through said second pair of holes for engagement with the lower vertebra.

12. The system of claim 1, wherein said plurality of holes are configured to facilitate insertion of one or more bone engaging fasteners through said insertion instrument and said plate into engagement with said vertebrae.

13. The system of claim 1, wherein said retaining element is positioned equidistant between said upper and lower ends of said plate body and equidistant between opposite sides of said plate body.

14. A system for providing spinal stabilization, comprising:
an implant including a body extending from a leading end to an opposite trailing end, said body including a superior bone engaging surface and an opposite inferior bone engaging surface, said superior and inferior bone engaging surfaces engaging respective endplates of upper and lower vertebrae when said implant is positioned in a spinal disc space between the upper and lower vertebrae;
a plate for engagement with the upper and lower vertebrae, said plate including a body extending between an upper end and an opposite lower end, said plate body including a proximal surface, an opposite distal surface, and a distal facing intermediate portion configured to cooperate with said trailing end of said implant, said plate including a plurality of holes and a retaining element rotatably disposed on an outer surface of said plate, said retaining element comprising a plurality of arms separated by gaps such that said retaining element is rotatable between a first position where said arms do not cover said plurality of holes and a second position where said arms cover said plurality of holes; and
an insertion instrument including an engaging portion configured to releasably engage with said implant and said plate, wherein said implant and said plate are held in a contiguous relationship when engaged by said instrument and said implant is displaceable from said plate upon disengagement of said instrument.

15. The system of claim 14, wherein said trailing end of said implant cooperates with said intermediate portion of said plate when said implant and said plate are held in said contiguous relationship.

16. The system of claim 15, wherein said trailing end of said implant is convexly rounded between said superior and inferior bone engaging surfaces and said intermediate portion of said plate includes a concave portion configured to receive at least a portion of said trailing end of said implant when said implant and said plate are held in said contiguous relationship.

17. The system of claim 16, wherein said concave portion of said intermediate portion is offset distally from portions of said distal surface at said upper and lower ends of said plate.

18. The system of claim 15, wherein said intermediate portion of said plate includes a convex portion, and said trailing end of said implant is concave between said superior and inferior bone engaging surfaces and configured to receive at least a portion of said intermediate portion of said plate when said implant and said plate are held in said contiguous relationship.

19. The system of claim 14, wherein an angular orientation of said implant relative to said plate is adjustable when said implant and said plate are held in said contiguous relationship by said instrument.

20. The system of claim 14, wherein said insertion instrument includes a plurality of guide holes configured to facilitate insertion of one or more bone engaging fasteners through said insertion instrument and said plate into engagement with said vertebrae.

21. A method for providing spinal stabilization between first and second vertebrae, comprising:
providing an implant including a body extending from a leading end to an opposite trailing end, said body including a superior bone engaging surface and an opposite inferior bone engaging surface;
providing a plate for engagement with the first and second vertebrae, said plate including a body extending between an upper end and an opposite lower end, said plate including a plurality of holes and a retaining element rotatably disposed on an outer surface of said plate, said retaining element comprising a plurality of arms separated by gaps such that said retaining element is rotatable between a first position where said arms do not cover said plurality of holes and a second position where said arms cover said plurality of holes;

engaging an insertion instrument with said implant and said plate, said engaging including retaining said implant and said plate in a contiguous, uncoupled arrangement; and inserting said leading end of said implant in a spinal disc space between the first and second vertebrae with said insertion instrument and advancing said implant into the disc space until a bottom surface of said plate contacts extradiscal surfaces of the first and second vertebrae.

22. The method of claim 21, which further includes rotating said implant relative to said plate when said insertion instrument is engaged with said implant and said plate and said implant and said plate are retained in said contiguous, uncoupled arrangement.

23. The method of claim 21, which further includes:

engaging said upper end of said plate to the first vertebra with at least one fastener and said lower end of said plate to the second vertebra with at least one fastener; and disengaging said insertion instrument from said plate and said implant, wherein said disengaging allows displacement of said implant away from said plate.

* * * * *